(12) United States Patent
Schrodt

(10) Patent No.: US 8,043,325 B2
(45) Date of Patent: Oct. 25, 2011

(54) LOADING DEVICE FOR DELIVERING AN EMBOLIZATION COIL INTO A MICROCATHETER

(75) Inventor: Benjamin Taylor Schrodt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 357 days.

(21) Appl. No.: 12/336,586

(22) Filed: Dec. 17, 2008

(65) Prior Publication Data

US 2010/0152650 A1   Jun. 17, 2010

(51) Int. Cl.
*A61M 29/00* (2006.01)
(52) U.S. Cl. .................................................. 606/200
(58) Field of Classification Search .............. 606/200; 604/264, 57; 623/1.11, 1.12, 1.23
See application file for complete search history.

(56) References Cited

U.S. PATENT DOCUMENTS

| | | | |
|---|---|---|---|
| 5,066,277 A * | 11/1991 | Carrell et al. .................. 604/110 |
| 5,163,903 A * | 11/1992 | Crittenden et al. ...... 604/103.09 |
| 5,350,397 A * | 9/1994 | Palermo et al. ................. 606/200 |
| 5,382,260 A | 1/1995 | Dormandy, Jr. et al. |
| 5,476,472 A * | 12/1995 | Dormandy et al. ............. 606/151 |
| 5,707,389 A * | 1/1998 | Louw et al. .................... 606/200 |
| 5,746,734 A | 5/1998 | Dormandy, Jr. et al. |
| 5,782,810 A | 7/1998 | O'Donnell |
| 5,891,130 A * | 4/1999 | Palermo et al. .................... 606/1 |
| 5,895,410 A * | 4/1999 | Forber et al. ................... 606/200 |
| 5,947,994 A | 9/1999 | Louw et al. |
| 5,984,944 A * | 11/1999 | Forber ........................... 606/191 |
| 6,033,413 A | 3/2000 | Mikus et al. |
| 6,096,022 A * | 8/2000 | Laymon et al. ............... 604/523 |
| 6,178,968 B1 | 1/2001 | Louw et al. |
| 6,203,547 B1 * | 3/2001 | Nguyen et al. ................ 606/102 |
| 6,221,081 B1 | 4/2001 | Mikus et al. |
| 6,458,137 B1 * | 10/2002 | Klint ............................ 606/108 |
| 6,726,712 B1 * | 4/2004 | Raeder-Devens et al. ... 623/1.11 |
| 6,752,827 B2 | 6/2004 | Ross et al. |
| 6,942,688 B2 | 9/2005 | Bartholf et al. |
| 7,367,980 B2 * | 5/2008 | Kida et al. ..................... 606/108 |
| 2003/0153926 A1 | 8/2003 | Schmieding et al. |
| 2004/0097780 A1 * | 5/2004 | Otsuka .............................. 600/7 |
| 2004/0267281 A1 | 12/2004 | Harari et al. |
| 2005/0049609 A1 | 3/2005 | Gunderson et al. |
| 2007/0043421 A1 * | 2/2007 | Mangiardi et al. ........... 623/1.11 |
| 2007/0112361 A1 * | 5/2007 | Schonholz et al. ............ 606/151 |
| 2007/0142893 A1 * | 6/2007 | Buiser et al. .................. 623/1.11 |
| 2007/0287957 A1 * | 12/2007 | Magnuson et al. ......... 604/103.1 |
| 2008/0103581 A1 * | 5/2008 | Goto ............................ 623/1.11 |
| 2009/0054905 A1 * | 2/2009 | Levy ............................ 606/108 |

* cited by examiner

*Primary Examiner* — Gary Jackson
*Assistant Examiner* — Erin Colello
(74) *Attorney, Agent, or Firm* — Brinks Hofer Gilson & Lione

(57) ABSTRACT

In one embodiment of the present invention, a device for delivering an embolization coil into a microcatheter for deployment of the embolization coil from the microcatheter into a body vessel of a patient is provided. The device comprises a cannula that has a proximal portion extending to a distal portion. The cannula has a lumen formed through the proximal and distal portions. The distal portion has a distal tip that is formed from metal and is configured to interface with the microcatheter for advancing the embolization coil from the lumen into the microcatheter. The proximal portion is at least partially formed of a transparent material for viewing into the lumen to facilitate delivery of the embolization coil into the microcatheter.

20 Claims, 4 Drawing Sheets

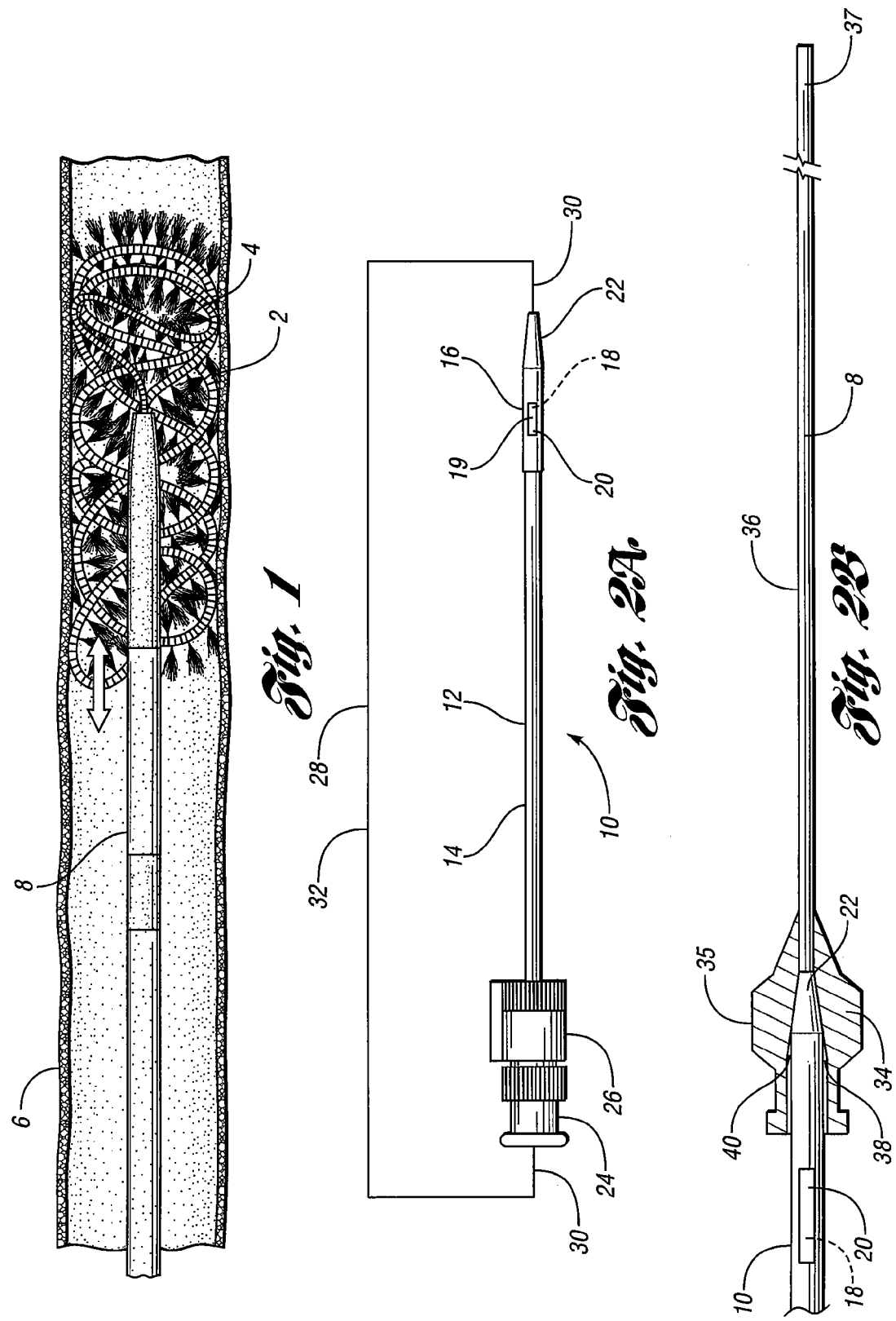

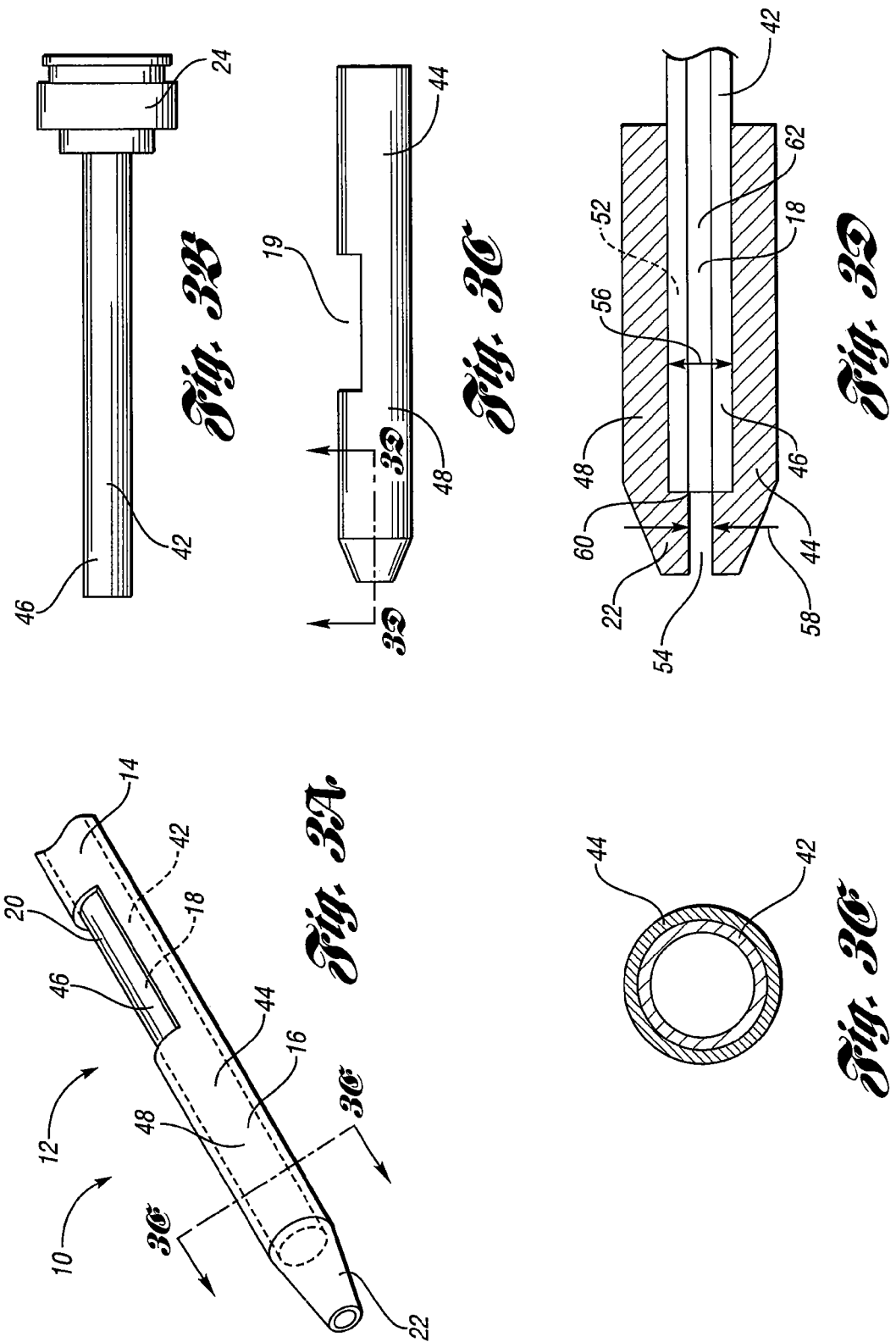

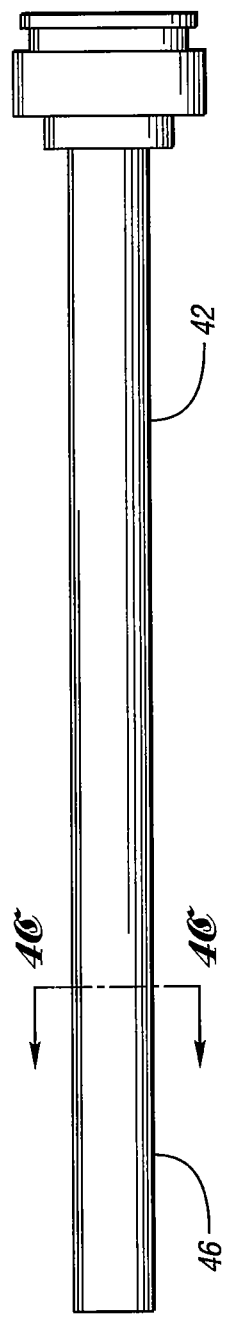
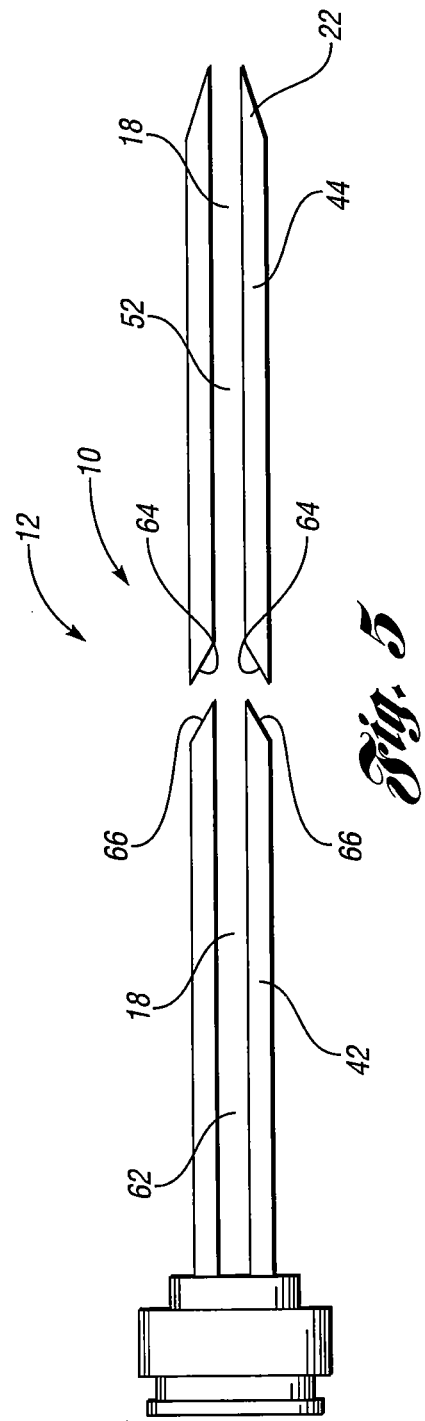
Fig. 4A.
Fig. 4B.
Fig. 4C.
Fig. 5.

LOADING DEVICE FOR DELIVERING AN EMBOLIZATION COIL INTO A MICROCATHETER

BACKGROUND OF THE INVENTION

1. Field of the Invention

The present invention relates to medical devices. More particularly, the invention relates to occluding devices for occluding fluid flow through a body vessel.

2. Background of the Invention

Embolization coils have been used to stop undesired blood flow, such as for example, in the treatment of aneurysms, arteriovenous malformations, traumatic fistulae and tumor embolization. These conditions require that the blood flow through a portion of a body vessel be stopped, for example by introducing an artificial device into the vessel to slow the flow, and by letting the natural clotting process form a more complete blockage of the blood vessel with a clot.

Embolization coils can be used to form a blockage in a vein or artery to treat conditions like those listed in the foregoing paragraph. These devices have become increasingly common in procedures to block the flow of blood by promoting formation of a clot in a desired location. Embolization coils may be made from a bio-compatible material, such as platinum, to minimize the problems associated with tissue irritation and rejection. These coils typically have a pre-coiled tension that correspondingly shapes the coil upon deployment as a complex three dimensional curvy structure that fill in portions of the body vessel and slow blood flow therein. Often, polymeric fibers are added to the metallic coils to enhance the coil's thrombogenicity, which is the coil's ability to promote formation of clots.

Embolization coils are typically introduced into a body vessel by using a microcatheter which extends from a proximal point outside of the patient's body to a distal point near the embolization site. A loading device, e.g., a metal introducer sheath or cannula, containing the embolization coil is used to carry and protect the coil prior to transferring the embolization coil to the microcatheter for introduction into the patient. Typically, the loading device may have a small metal stopper or wire stopper that is used to hold the embolization coil within the loading device during packaging and shipping. When the interventionalist is ready to transfer the embolization coil to the microcatheter, she removes the stopper to release the coil into the microcatheter. Sometimes, however, the embolization coil falls out of the loading device prior to being transferred to the microcatheter. If the interventionalist is unaware that the loading device is empty, the occluding procedure may be temporarily performed on the patient without using the embolization coil until the interventionalist realizes the mishap. This will prolong the procedure and possibly present an unnecessary risk to the patient. Accordingly, further improvements and enhances to a device for transferring an embolization coil to a microcatheter for introduction into a patient are desirable.

BRIEF SUMMARY OF THE INVENTION

In one embodiment of the present invention, a device for delivering an embolization coil into a microcatheter is provided. The microcatheter is used to deploy the embolization coil into a body vessel of a patient. The device comprises a cannula that has a proximal portion which extends to a distal portion. A lumen is formed through the proximal and distal portions of the cannula. The distal portion has a distal tip that is formed from metal and is configured to interface with the microcatheter for advancing the embolization coil from the lumen into the microcatheter. The proximal portion is at least partially formed of a transparent material for viewing into the lumen to facilitate delivering the embolization coil into the microcatheter.

In one aspect, the proximal portion of the cannula is at least partially formed of a transparent plastic material and the distal tip is tapered distally. The tapered distal tip is for interfacing with a tapered shaped hub of the microcatheter for advancing the embolization coil from the lumen of the cannula into the microcatheter.

In another embodiment of the present invention, an embolization kit for occluding fluid flow through a body vessel of a patient is provided. The kit comprises an embolization coil, a microcatheter and a device for delivering the embolization coil into the microcatheter as discussed in the foregoing paragraphs. The embolization coil has a pre-curled tension to facilitate the embolization coil curling within the body vessel when deployed. The microcatheter includes a hub and an elongated tube that extends distally from the hub. The elongated tube is configured to be positioned in the body vessel to deploy the embolization coil. The hub has a tapered wall that defines an opening for receiving the embolization coil and for advancing the embolization coil into the elongated tube.

Further objections, features, and advantages of the present invention will become apparent from consideration of the following description and the appended claims when taken in connection with the accompanying drawings.

BRIEF DESCRIPTION OF THE DRAWINGS

FIG. 1 a side view of an embolization coil being deployed from a microcatheter into a body vessel of a patient;

FIG. 2a is a side view of a device for delivering an embolization coil in accordance with one embodiment of the present invention;

FIG. 2b is a side view of a device delivering an embolization coil into a microcatheter in accordance to one embodiment of the present invention;

FIG. 3a is a perspective view of a distal portion of a device for delivering an embolization coil in accordance with one embodiment of the present invention;

FIG. 3b is a side view of a cannula section of the device depicted in FIG. 3a;

FIG. 3c is a side view of a metal sheath of the device depicted in FIG. 3a;

FIG. 3d is a sectional view of the metal sheath depicted in FIG. 3c;

FIG. 3e is a cross-sectional view of the device depicted in FIG. 3a;

FIG. 4a is a cannula section of a device for delivering an embolization coil in accordance with an embodiment of the present invention;

FIG. 4b is a metal sheath of a device for delivering an embolization coil in accordance with an embodiment of the present invention;

FIG. 4c is a cross-sectional view of the cannula section depicted in FIG. 4a;

FIG. 5 is an exploded side view of a device for delivering an embolization coil in accordance with one embodiment of the present invention.

DETAILED DESCRIPTION OF THE INVENTION

Figure 6:
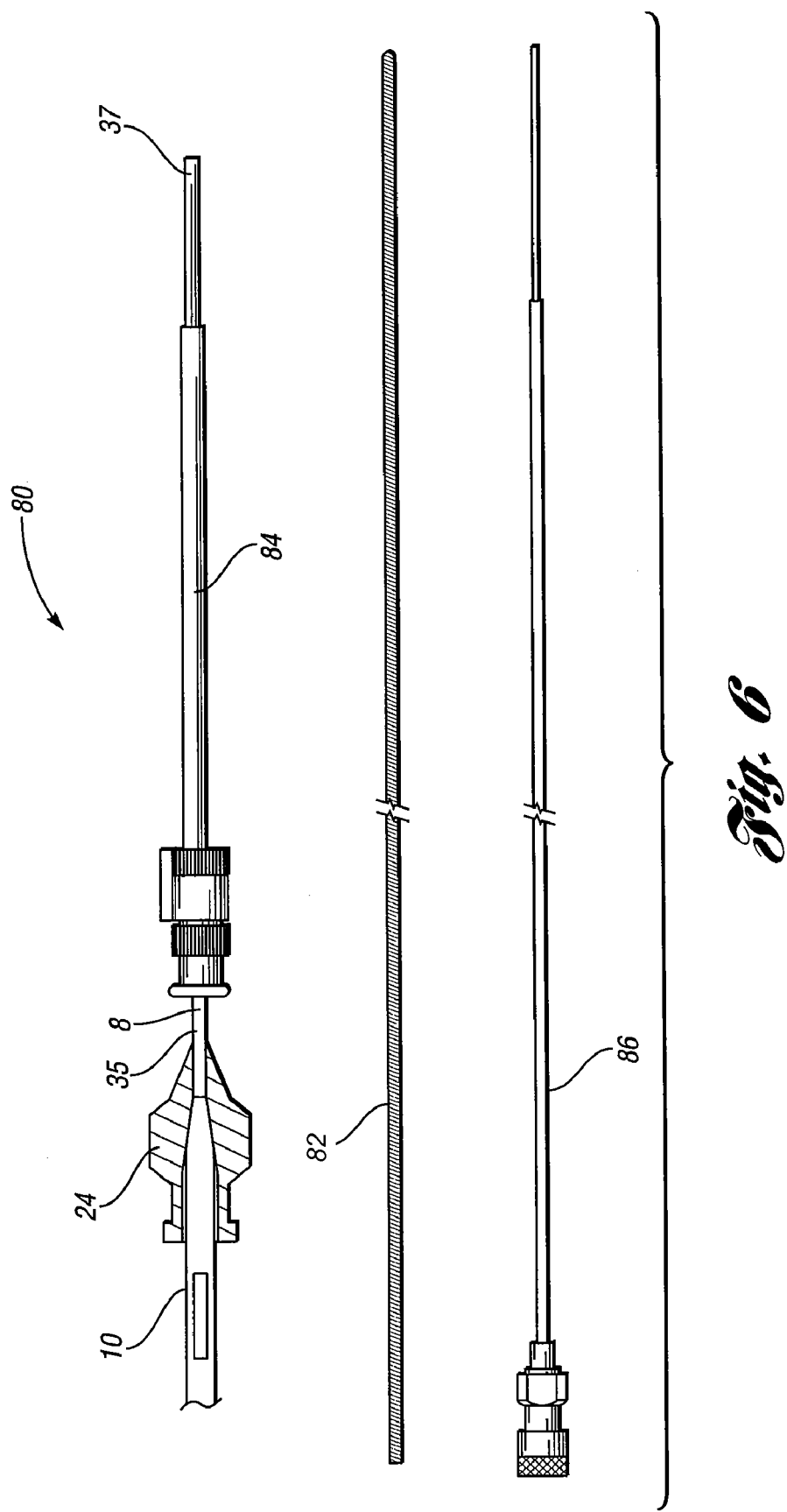
FIG. 6 is a side view of an embolization kit in accordance with an embodiment of the present invention.

Detailed embodiments of the present invention are disclosed herein. It is understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and teaching one skilled in the art to practice the present invention.

The present invention seeks to overcome some of the problems associated with delivering an embolization coil into a microcatheter for introduction into a body vessel of a patient. Preferably, the present invention provides a device for carrying the embolization coil and for delivering the embolization coil into a microcatheter that facilitates an interventionalist being able to detect whether an embolization coil is present in the device or, for example, has accidentally fallen out of the device. More specifically, the device has a lumen for carrying the embolization coil and for advancing the embolization coil from the device. The device also has a transparent section surrounding at least a portion of the lumen that allows the interventionalist to view into the lumen to determine whether or not the embolization coil is present within the device prior to and/or during delivery of the embolization coil into the microcatheter.

Referring to FIG. 1, multiple embolization coils 2 and 4 may be used to occlude a body vessel 6 of a patient. The embolization coils 2 and 4 are deployed into the body vessel 6 from a microcatheter 8. In this embodiment, a high radial force embolization coil 2 is initially deployed within the body vessel 6 to form an embolization anchor within the body vessel 6. The relatively high radial force of the anchoring coil 2 pushes against the wall of the body vessel 6 to resist further advancement through the body vessel 6 from forces generated by arterial blood flow.

Subsequently, a soft embolization coil 4 (e.g. relatively intermediate or low radial force) is deployed adjacent to the high radial force embolization coil 2 to fill in various gaps that may exist between the curled configuration of the high radial force embolization coil 2. Various weaving or moving techniques may be used to deploy the embolization coils 2 and 4, such as for example, a coaxial technique to prevent coil elongation, a scaffold technique or an anchor technique. Other suitable techniques known to those skilled in the art for deploying embolization coils may also be used. Preferably, sufficient arterial blood flow remains to hold the soft embolization coil 4 against the anchoring embolization coil 2 until a solid clot ensures a permanent fixation.

Referring to FIG. 2a, a device 10 for delivering an embolization coil 2 and 4 into a microcatheter 8 for deployment therefrom is provided. The device 10 comprises a cannula 12. The cannula 12 has a proximal portion 14 that extends to a distal portion 16. A lumen 18 is formed through the cannula 12 extending through the proximal and distal portions 14 and 16. The cannula 12 is used to carry and protect the embolization coil 2 and 4, which is contained in the lumen 18, prior to being transferred into the microcatheter 8.

Referring also to FIG. 2b, the distal portion 16 has a distal tip 22 that interfaces with the microcatheter 8 for advancing the embolization coil 2 and 4 from the lumen 18 into the microcatheter 8. In one example, the microcatheter 8 has a hub 34, which may be made from a transparent material, at its proximal end 35 and an elongated tube 36 that extends distally from the hub 34 for positioning in the body vessel 6. The hub 34 has a tapered wall 38 that defines an opening 40 for receiving the distal tip 22 and for transferring the embolization coil 2 and 4 from the device 10. The distal tip 22 is preferably tapered distally to match the tapered wall 38 of the hub 34 to facilitate a tight engagement with the microcatheter 8. Once received, the embolization coil 2 and 4 is advanced into the elongated tube 36.

In one embodiment, the distal tip 22 is formed from metal, e.g., stainless steel. Preferably, the relatively high strength of the metal that forms the thinly tapered distal tip 22 provides sufficient structure to the distal tip 22 for being forcibly engaged with the microcatheter 8 without breaking or becoming deformed to ensure proper transfer of the embolization coil 2 and 4 into the microcatheter 8.

Proximal the distal tip 22, the cannula 12 is at least partially formed from a transparent material, e.g., amorphous plastic such as clear polycarbonate or a semi-crystalline plastic such as a relatively clear, translucent polyamide. In one example, the transparent material forms the proximal portion 14 and part of the distal portion 16, which is also covered by the metal material that extends proximally from the distal tip 22. An opening 19 may be formed in the metal overlying the transparent material to form a window 20 for viewing through the transparent material into the lumen 18 to facilitate delivery of the embolization coil 2 and 4 into the microcatheter 8.

The device 10 may further include a hub 24 that is disposed opposite the distal tip 22 at the proximal end of the proximal portion 14. Adjacent to the hub 24, the device 10 may also include an adjustable luer fitting 26. The fitting 26 may be advanced along the cannula 12 between the hub 24 and the distal tip 22 and is rotatable to couple with the hub 34 of the microcatheter 8. Coupling the cannula 12 with the microcatheter 8 preferably stabilizes the device 10 with the microcatheter 8 ensuring proper transfer of the embolization coil 2 and 4.

A stopper 28, e.g., a wire stopper, may be used to keep the embolization coil 2 and 4 within the device 10. In one example, ends 30 of the wire stopper 28 corresponding obstruct the proximal and distal ends of the lumen 18. A stopper body 32 that extends between the ends 30 is disposed outside the device 10 where it may be manipulated by the interventionalist to remove the ends 30 from the lumen 18 to release the embolization coil 2 and 4 contained therein.

Referring to FIGS. 3a-3e is at least one embodiment for the device 10. The cannula 12 comprises a clear cannula section 42 and a metal sheath 44. The metal sheath 44 is disposed adjacent to a distal end portion 46 of the clear cannula section 42. The metal sheath 44 forms at least part of the distal portion 16 of the cannula 12 and includes the distal tip 22. The clear cannula section 42 forms at least part of the proximal portion 14 of a cannula 12. In one example, the clear cannula section 42 and the metal sheath 44 are affixed together, e.g., via glue or adhesive.

In one embodiment, the metal sheath 44 has an outer perimeter body 48 that extends proximally from the distal tip 22. The outer perimeter body 48 may be relatively thin and disposed about at least a distal end portion 46 of the clear cannula section 42. This configuration may provide a relatively large surface area for bonding the metal sheath 44 to the clear cannula section 42 and further enhance the structure of the cannula 12 by providing a layered composite structure (see FIG. 3e). In one example, the outer perimeter body 48 substantially covers the length of the cannula section 42 adjacent to the hub 24.

In this embodiment, the window 20 as discussed in the foregoing paragraphs may be defined by an opening 19 formed in the metal sheath 44. The opening 19 overlies the distal end portion 46 of the clear cannula section 42 to form the window 20 for viewing into the lumen 18.

The outer perimeter body 48 of the metal sheath 44 has a proximal lumen 52 formed therethrough. The distal tip 22 of the metal sheath 44 has a distal lumen 54 formed therethrough that extends to the proximal lumen 52. In one example, the proximal lumen 52 has a larger diameter 56 relative to a diameter 58 of the distal lumen 58 such that a step 60 is formed in the metal sheath 44 adjacent to where the proximal and distal lumens 52 and 54 intersect. The distal end portion 46 of the clear cannula section 42 is positioned in the proximal lumen 52 so as to be contiguous with the step 60. The clear cannula section 42 has a lumen 62 that is aligned with the distal lumen 54 of the distal tip 22 to define the lumen 18 of the cannula 12.

FIGS. 4a-4c illustrate an embodiment similar to the embodiments depicted in FIGS. 3a-3e except for the following. The outer perimeter body 48 of the metal sheath 44 may have a relatively short length that covers only the distal end portion 46 of the clear cannula section 42. As such, no opening may be formed in the outer perimeter body 48 that defines a window for viewing into the lumen 18. Rather, because of the relatively short length of the outer perimeter body 48, a substantial length along the clear cannula section 42 is available to provide the interventionalist with visual contact with the lumen 18. Preferably, sufficient surface area between the clear cannula section 42 and the outer perimeter body 48 is available to provide for suitable bonding therebetween.

FIG. 5 illustrates another embodiment similar to the embodiments depicted in FIGS. 4a-4c except for the following. In this case, the metal sheath 44 abuts the clear cannula section 42 at corresponding proximal and distal ends 64 and 66. In one example, the ends 64 and 66 are bonded together to form the cannula 12. The metal sheath 44 and the clear cannula section 42 have substantially the same size lumens 52 and 62 that are aligned to form the lumen 18 of the cannula 12.

FIG. 6 illustrates at least one embodiment of an embolization kit 80. As shown, the kit 80 includes a microcatheter 8, preferably made from a soft, flexible material such as silicone or any other suitable material. Generally, the microcatheter 8 has a proximal end 35, a distal end 37, and a plastic adapter or hub 24 to receive an embolization coil 2 and 4 from the delivery device 10. In this embodiment, the inside diameter of the microcatheter 8 may range between 0.014 and 0.027 inches.

The kit 80 may further include a guide wire 82 which provides a guide catheter 84 a path during insertion of the guide catheter 84 within the body vessel 6. The size of the guide wire 82 is based on the inside diameter of the guide catheter 84.

The kit 80 further includes a polytetrafluoroethylene (PTFE) guide catheter 84 or sheath for percutaneously introducing the microcatheter 8 into the body vessel 6. Of course, any other suitable material may be used without falling beyond the scope or spirit of the present invention. The guide catheter 84 may have a size between about 4-French to 8-French and allows the microcatheter 8 to be inserted therethrough to a desired location in the body vessel 6. The guide catheter 84 receives the microcatheter 8 and provides stability of the microcatheter 8 at a desired location within the body vessel 6. For example, the guide catheter 84 may stay stationary within a common visceral artery, e.g., a common hepatic artery, and add stability to the microcatheter 8 as the microcatheter 8 is advanced through the guide catheter 84 to a point of occlusion in the connecting artery, e.g., the left or right hepatic artery.

When the distal end 37 of the microcatheter 8 is at a point of occlusion in the body vessel 6, the embolization coil 2 and 4 is loaded from the delivery device 10 at the proximal end 35 of the microcatheter and the embolization coil 2 and 4 is advanced through the microcatheter 8 for deployment through the distal end 37. In this embodiment, a push wire 86 is used to mechanically advance or push the embolization coil 2 and 4 through the microcatheter 8. The size of the push wire 86 depends on the diameter of the microcatheter 8. As mentioned above, when the embolization coil 2 and 4 is deployed in the body vessel 6, and anchoring embolization coil 2 may serve to hold in place against the inner wall of the body vessel 6 and subsequently softer embolization coils 4 (e.g. made from platinum) with fibers may be further deployed to serve to occlude fluid flow by filling the lumen of the body vessel 6.

In an alternative embodiment, an elongated releasing member (not shown) may be used instead of a push wire 86. The elongated releasing member is similar to the push wire 86 in that it may be advanced through the microcatheter 8 to deploy the embolization coil 2 and 4 through the distal end 37. However, the elongated releasing member further includes a distal end configured for selectively engaging with the embolization coil 2 and 4. For example, the distal end of the elongated releasing member may have threads which engage with the wire windings of an embolization coil 2 and 4. Once the embolization coil 2 and 4 is deployed through the microcatheter 8, the elongated releasing member may be twisted or unscrewed to disengage the embolization coil 2 and 4 from the elongated releasing member, thus releasing the embolization coil 2 and 4 within the body vessel 6. Other suitable releasing devices known to those skilled in the art may be used to advance and selectively deploy the embolization coil 2 and 4 from the microcatheter 8.

It is to be understood that the body cavity embolization kit described above is merely one example of a kit that may be used to deploy an embolization coil in a body vessel. Of course, other kits, assemblies, and systems may be used to deploy an embodiment of the embolization coil without falling beyond the scope or spirit of the present invention.

As a person skilled in the art will readily appreciate, the above description is meant as an illustration of the implementation of the principles of this invention. This description is not intended to limit the scope or application of this invention in that the invention is susceptible to modification, variation, and change, without departing from the spirit of this invention as defined in the following claims.

I claim:

1. A device for delivering an embolization coil into a microcatheter for deployment of the embolization coil from the microcatheter into a body vessel of a patient, the device comprising:
 a cannula having a proximal portion extending to a distal portion, the cannula having a first lumen formed through the proximal and distal portions, the proximal portion of the cannula comprising a non-tapered cannula section having a proximal end portion and a distal end portion, the non-tapered cannula section having a second lumen formed through the proximal end portion and the distal end portion, the distal portion of the cannula comprising a metal sheath extending distally from the distal end portion of the non-tapered cannula section, the metal sheath having a tapered distal tip to interface with the microcatheter, the non-tapered cannula section being at least partially formed of a transparent plastic material for viewing into the second lumen to facilitate delivery of the embolization coil into the microcatheter; and
 an embolization coil disposed in the second lumen of the non-tapered cannula section, wherein the entire embolization coil is disposed in the second lumen of the non-tapered cannula section.

2. The device according to claim 1 wherein the non-tapered cannula section is a clear cannula section.

3. The device according to claim 2 wherein the clear cannula section and the metal sheath are affixed together.

4. The device according to claim 2 wherein the metal sheath further comprises a tip portion and an outer perimeter body that extends proximally from the tip portion, the tip portion of the metal sheath defining the tapered distal tip, and the outer perimeter body being disposed about the distal end portion of the clear cannula section.

5. The device according to claim 4 wherein the outer perimeter body of the metal sheath defines an opening for viewing into the first lumen of the cannula.

6. The device according to claim 4 wherein the outer perimeter body of the metal sheath has a proximal lumen and the tip portion of the metal sheath has a distal lumen that extends from the proximal lumen, the proximal lumen has a larger diameter relative to a diameter of the distal lumen such that a step is formed in the metal sheath adjacent to where the proximal and distal lumens intersect, the distal end portion of the clear cannula section is disposed in the proximal lumen contiguous with the step, and the second lumen of the clear cannula section is aligned with the distal lumen of the tip portion, defining the first lumen of the cannula.

7. The device according to claim 4 wherein the outer perimeter body of the metal sheath is further disposed about the proximal end portion of the clear cannula section.

8. The device according to claim 2 wherein the clear cannula section abuts the metal sheath to form the cannula.

9. The device according to claim 2 wherein the clear cannula section abuts the metal sheath to form the cannula.

10. A device for delivering an embolization coil into a microcatheter for deployment of the embolization coil from the microcatheter into a body vessel of a patient, the device comprising:
a cannula having a proximal portion extending to a distal portion, the cannula having a first lumen formed through the proximal and distal portions, the proximal portion of the cannula comprising a non-tapered cannula section having a proximal end portion and a distal end portion, the non-tapered cannula section having a second lumen formed through the proximal end portion and the distal end portion, the distal portion of the cannula comprising a metal sheath extending distally from the distal end portion of the non-tapered cannula section, the metal sheath having a distal tip that is configured to interface with the microcatheter, the non-tapered cannula section being at least partially formed of a transparent material for viewing into the second lumen to facilitate delivery of the embolization coil into the microcatheter; and
an embolization coil disposed in the second lumen of the non-tapered cannula section, wherein the entire embolization coil is disposed in the second lumen of the non-tapered cannula section.

11. The device according to claim 10 wherein the non-tapered cannula section is a clear cannula section.

12. The device according to claim 11 wherein the metal sheath further comprises a tip portion and an outer perimeter body that extends proximally from the tip portion, the tip portion of the metal sheath defining the distal tip, and the outer perimeter body being disposed about the distal end portion of the clear cannula section.

13. The device according to claim 12 wherein the outer perimeter body of the metal sheath defines an opening for viewing into the first lumen of the cannula.

14. The device according to claim 12 wherein the outer perimeter body of the metal sheath has a proximal lumen and the tip portion of the metal sheath has a distal lumen that extends from the proximal lumen, the proximal lumen has a larger diameter relative to a diameter of the distal lumen such that a step is formed in the metal sheath adjacent to where the proximal and distal lumens intersect, the distal end portion of the clear cannula section is disposed in the proximal lumen contiguous with the step, and the second lumen of the clear cannula section is aligned with the distal lumen of the tip portion, defining the first lumen of the cannula.

15. An embolization kit for occluding fluid flow through a body vessel of a patient, the kit comprising:
an embolization coil having a pre-curled tension to facilitate the embolization coil to be curled within the body vessel when deployed;
a microcatheter including a hub and an elongated tube that extends distally from the hub, the elongated tube being configured to be positioned in the body vessel to deploy the embolization coil, the hub having a tapered wall that defines an opening for receiving the embolization coil and for advancing the embolization coil into the elongated tube;
a device for delivering the embolization coil into the microcatheter, the device including:
a cannula having a proximal portion extending to a distal portion, the cannula having a first lumen formed through the proximal and distal portions, the proximal portion of the cannula comprising a non-tapered cannula section having a proximal end portion and a distal end portion, the non-tapered cannula section having a second lumen formed through the proximal end portion and the distal end portion, the distal portion of the cannula comprising a metal sheath extending distally from the distal end portion of the non-tapered cannula section, the metal sheath having a distal tip that is tapered distally to interface with the tapered wall of the hub of the microcatheter, the non-tapered cannula section being at least partially formed of a transparent plastic material for viewing into the second lumen to facilitate delivery of the embolization coil into the microcatheter; wherein the entire embolization coil is disposed in the second lumen of the non-tapered cannula section.

16. The kit according to claim 15 wherein the non-tapered cannula section is a clear cannula section.

17. The kit according to claim 15 wherein the metal sheath further comprises a tip portion and an outer perimeter body that extends proximally from the tip portion, the tip portion of the metal sheath defining the distal tip, and the outer perimeter body being disposed about the distal end portion of the clear cannula section.

18. The kit according to claim 15 further comprising a guide catheter, the microcatheter being configured to be passed through the guide catheter to position the microcatheter in the body vessel.

19. The kit according to claim 18 further comprising a guide wire for guiding the guide catheter in the body vessel.

20. The kit according to claim 15 further comprising one of a pusher wire and an elongated releasing member for advancing the embolization coil through the microcatheter for deployment within the body vessel.

* * * * *